US006262105B1

(12) United States Patent
Johnstone

(10) Patent No.: US 6,262,105 B1
(45) Date of Patent: Jul. 17, 2001

(54) METHOD OF ENHANCING HAIR GROWTH

(76) Inventor: Murray A. Johnstone, 1221 Madison, #1124, Seattle, WA (US) 98104

( * ) Notice: Subject to any disclaimer, the term of this patent is extended or adjusted under 35 U.S.C. 154(b) by 0 days.

(21) Appl. No.: 09/366,656

(22) Filed: Aug. 3, 1999

Related U.S. Application Data

(63) Continuation of application No. PCT/US98/02289, filed on Feb. 3, 1998.
(60) Provisional application No. 60/037,237, filed on Feb. 4, 1997.

(51) Int. Cl.[7] .......................... A61K 31/38; A61K 31/215
(52) U.S. Cl. .......................... 514/430; 514/530; 514/880
(58) Field of Search ...................................... 514/430, 530

(56) References Cited

U.S. PATENT DOCUMENTS

| | | |
|---|---|---|
| 4,139,619 | 2/1979 | Chidsey, III . |
| 4,311,707 | 1/1982 | Birnbaum et al. . |
| 4,599,353 | 7/1986 | Bito . |
| 4,883,819 | 11/1989 | Bito . |
| 4,952,581 | 8/1990 | Bito et al. . |
| 4,968,812 | 11/1990 | Wang et al. . |
| 5,288,754 | 2/1994 | Woodward et al. . |
| 5,321,128 | 6/1994 | Stjernschantz et al. . |
| 5,352,708 | 10/1994 | Woodward et al. . |
| 5,422,368 | 6/1995 | Stjernschantz et al. . |
| 5,422,369 | 6/1995 | Stjernschantz et al. . |
| 5,578,618 | 11/1996 | Stjernschantz et al. . |

FOREIGN PATENT DOCUMENTS

| | | |
|---|---|---|
| 0 170 258 | 2/1986 | (EP) . |
| 0 253 094 | 1/1988 | (EP) . |
| 0 308 135 | 3/1989 | (EP) . |
| 89/03384 | 4/1989 | (WO) . |
| 95/11003 | 4/1995 | (WO) . |
| 98/33497 | 8/1998 | (WO) . |

OTHER PUBLICATIONS

Alm, A. et al., Phase III Latanoprost Studies in Scandinavia, the United Kingdom and the United States, *Surv. Ophthalmol.* 41(Suppl. 2):S105–S110 (1997).
Bito, L.Z. et al., "Long–term Maintenance of Reduced Intraocular Pressure by Daily or Twice Daily Topical Application of Prostaglandins to Cat or Rhesus Monkey Eyes," *Invest. Ophthalmol. Vis. Sci.* 24(3):312–319 (1983).
Camras, C.B. et al., "Reduction of intraocular pressure in normal and glaucomatous primate (*Aotus trivirgatus*) eyes by topically applied prostaglandin $F_{2\alpha}$," *Current Eye Res.* 1(4): 205–209 (1981).
Camras, C.B. et al., "Multiple Dosing of Prostaglandin $F_{2\alpha}$ or Epinephrine on Cynomolgus Monkey Eyes," *Invest. Ophthalmol. Vis. Sci.* 28(3):463–469 (1987).
Camras, C.B. et al., "Multiple Dosing of Prostaglandin $F_{2\alpha}$ or Epinephrine on Cynomolgus Monkey Eyes," *Invest. Ophthalmol. Vis. Sci.* 28(6):921–926 (1987).
Camras, C.B. et al., "Multiple Dosing of Prostaglandin $F_{2\alpha}$ or Epinephrine on Cynomolgus Monkey Eyes," *Invest Ophthalmol. Vis. Sci.* 29(9):1428–1436 (1988).
Camras, C.B., Comparison of Latanoprost and Timolol in Patients with Ocular Hypertension and Glaucoma, *Ophthalmology* 103(1):138–147 (1996).
Camras, C.B. et al., "Latanoprost, a Prostaglandin Analog, for Glaucoma Therapy," *Ophthalmology* 103(11):1916–1924 (1996).
Giuffrè, G., The effects of prostaglandin $F_{2\alpha}$ in the human eye, *Graefe's Arch. Clin. Exp. Ophthalmol.* 222:139–141 (1985).
Kaufman, P.L., "Effects of Intracamerally Infused Prostaglandins on Outflow Facility in Cynomolgus Monkey Eyes with Intact or Retrodisplaced Ciliary Muscle," *Exp. Eye Res.* 43:819–827 (1986).
Kerstetter, J.R., et al., "Prostaglandin $F_{2\alpha}$–1–Isopropylester Lowers Intraocular Pressure Without Decreasing Aqueous Humor Flow," *Am. J. Ophthalmol.* 105(1):30–34 (1988).
Lee, P.–Y, et al., "The Effect of Prostaglandin $F_{2\alpha}$ on Intraocular Pressure in Normotensive Human Subjects," *Invest. Ophthalmol. Vis. Sci.* 29(10):1474–1477 (1988).
Villumsen, J. et al., "Prostaglandin $F_{2\alpha}$–isopropylester eye drops: effect on intraocular pressure in open–angle glaucoma," *Br. J. Ophthalmol.* 73:975–979 (1989).
Mishima, H.K. et al., "A Comparison of Latanoprost and Timolol in Primary Open–angle Glaucoma and Ocular Hypertension," *Arch. Ophthalmol.* 114:929–932 (1996).
Alm, A. et al., "Effects on Intraocular Pressure and Side Effects of 0.005% Lantanoprost Applied Once Daily, Evening or Morning," *Ophthalmology* 102(12):1743–1752 (1995).
Darnell, J. et al., "Cell–to–Cell Signaling: Hormones and Receptors," *Molecular Cell Biology* (Darnell, J., Lidish, H., Baltimore, D., Eds.), W.H. Freeman and Company, New York, New York, pp. 738–743 (1990).
Fagot, D., et al., "Mitogenic Signaling by Prostaglandins in Chemically Transformed Mouse Fibroblasts: Comparison with Phorbol Esters and Insulin," *Endocrinology* 132(4):1729–1734 (1993).
Jimenez de Asua, L. et al., "The Stimulation of the Initiation of DNA Synthesis and Cell Division in Swiss Mouse 3T3 Cells by Prostaglandin $F_{2\alpha}$ Requires Specific Functional Groups in the Molecule," *J. Biol. Chemistry* 256(14):8774–8780 (1983).

(List continued on next page.)

*Primary Examiner*—Rebecca Cook
(74) *Attorney, Agent, or Firm*—Christensen O'Connor Johnson Kindness PLLC

(57) ABSTRACT

Methods and compositions for stimulating the growth of hair are disclosed containing prostaglandins, derivatives or analogues thereof for use in treating the skin or scalp of a human or non-human animal. Prostaglandins of the $A_2$, $F_2\alpha$ and $E_2$ types are preferred for this treatment method.

9 Claims, No Drawings

OTHER PUBLICATIONS

Houssay, A.B., et al., "Effects of Prostaglandins Upon Hair Growth in Mice," *Acta. Physiol. Lat. Am.* 26(3):186–91 (1976).

Resul, B. et al., "Structure–Activity Relationships and Receptor Profiles of Some Ocular Hypotensive Prostanoids," *Survey of Ophthalmol.* 41(Suppl. 2):S47–S52 (1997).

Database REGISTRY on STN, American Chemical Society, RN 135646–98–9, '5–Heptenoic acid, 7-[3, 5–dihydroxy–2–(3–oxo–5–phenylpentyl)cyclopentyl]–,1 methylethyl ester, [1R-[1,alpha.(Z),2.beta.,3.alpha.,5.alpha.]]-' abstract (1991).

Database WPIDS on STN, Derwent Information Ltd., AN 86–295722 [45], JP 61218510 A (Daichi Seiyaku Co), abstract., 1986.

METHOD OF ENHANCING HAIR GROWTH

This application is a continuation of international application number PCT/US98/02289, filed Feb. 3, 1998, and claims the benefit of provisional application No. 60/037,237, filed Feb. 4, 1997, priority from the filing dates of which is hereby claimed under 35 U.S.C. §§ 119 and 120.

FIELD OF THE INVENTION

This invention relates to a process for stimulating the growth of mammalian hair comprising the application to mammalian skin of prostaglandin compounds, derivatives and analogues and the pharmacologically acceptable acid addition salts thereof, alone or in association with a topical pharmaceutical carrier.

More particularly, the invention is concerned with the use of prostaglandin derivatives of PGA, PGE and PGF for the stimulation of hair growth. The invention relates also to therapeutic compositions, containing an active amount of these prostaglandin derivatives, and the manufacture of such compositions.

BACKGROUND OF THE INVENTION

Dermatologists recognize many different types of hair loss, the most common by far being "alopecia" wherein human males begin losing scalp hair at the temples and on the crown of the head as they get older. While this type of hair loss is largely confined to males, hence its common name "male pattern baldness," it is not unknown in women. Be that as it may, no known cure has yet been found despite continuing attempts to discover one.

Notwithstanding the fact that nothing heretofore has been found which is effective in preventing, yet alone reversing, male pattern baldness, a good deal is known about various types of human hair and its growth patterns on various parts of the body.

For purposes of the present invention, we need consider various types of hair, including, terminal hairs and vellus hairs and modified terminal hairs, such as seen in eye lashes and eye brows. Terminal hairs are coarse, pigmented, long hairs in which the bulb of the hair follicle is seated deep in the dermis. Vellus hairs, on the other hand, are fine, thin, non-pigmented short hairs in which the hair bulb is located superficially in the dermis. As alopecia progresses, a transition takes place in the area of approaching baldness wherein the hairs themselves are changing from the terminal to the vellus type.

Another factor that contributes to the end result is a change in the cycle of hair growth. All hair, both human and animal, passes through a life cycle that includes three phases, namely, (1) the anagen phase (2) the catagen phase and (3) the telogen phase. The anagen phase is the period of active hair growth and, insofar as scalp hair is concerned, this generally lasts from 3–5 years. The catagen phase is a short transitional phase between the anagen and telogen phases which, in the case of scalp hair, lasts only 1–2 weeks. The final phase is the telogen phase which, for all practical purposes, can be denominated a "resting phase" where all growth ceases and the hair eventually is shed preparatory to the follicle commencing to grow a new one. Scalp hair in the telogen phase is also relatively short-lived, some 3–4 months elapsing before the hair is shed and a new one begins to grow.

Under normal hair growth conditions on the scalp, approximately 88% of the hairs are in the anagen phase, only 1% in catagen and the remainder in telogen. With the onset of male pattern baldness, a successively greater proportion of the hairs are in the telogen phase with correspondingly fewer in the active growth anagen phase.

The remaining result associated with alopecia is the severe diminution of hair follicles. A bald human subject will average only about 306 follicles per square centimeter, whereas, a non-bald one in the same age group (30–90 years) will still have an average of 460 follicles per square centimeter. This amounts to a one-third reduction in hair follicles which, when added to the increased proportion of vellus hair follicles and the increased number of hair follicles in telogen, is both significant and noticeable. It is written that approximately 50% of the hairs must be shed to produce visible thinning of scalp hair. It is thus a combination of these factors: (1) transition of hairs from terminal to vellus, (2) increased number of telogen hairs—some of which have been shed, and (3) loss of hair follicles (atrophy) that produces "baldness".

While a good deal is known about the results of male pattern baldness, very little is known about its cause. The cause is generally believed to be genetic and hormonal in origin although, as will be seen presently, the known prior art attempts to control it through hormone adjustment have been singularly unsuccessful.

One known treatment for male pattern alopecia is hair transplantation. Plugs of skin containing hair are transplanted from areas of the scalp where hair is growing to bald areas with reasonable success; however, the procedure is a costly one in addition to being time-consuming and quite painful. Furthermore, the solution is inadequate from the standpoint that it becomes a practical, if not an economic, impossibility to replace but a tiny fraction of the hair present in a normal healthy head of hair.

Other non-drug related approaches to the problem include such things as ultra-violet radiation, massage, psychiatric treatment and exercise therapy. None of these, however, has been generally accepted as being effective. Even such things as revascularization surgery and acupuncture have shown little, if any, promise.

By far, the most common approach to the problem of discovering a remedy for hair loss and male pattern alopecia has been one of drug therapy. Many types of drugs ranging from vitamins to hormones have been tried and only recently has there been any indication whatsoever of even moderate success. For instance, it was felt for a long time that since an androgenic hormone was necessary for the development of male pattern baldness, that either systemic or topical application of an antiandrogenic hormone would provide the necessary inhibiting action to keep the baldness from occurring. The theory was promising but the results were uniformly disappointing.

The androgenic hormone testosterone was known, for example, to stimulate hair growth when applied topically to the deltoid area as well as when injected into the beard and pubic regions. Even oral administration was found to result in an increased hair growth in the beard and pubic areas as well as upon the trunk and extremities. While topical application to the arm causes increased hair growth, it is ineffective on the scalp and some thinning may even result. Heavy doses of testosterone have even been known to cause male pattern alopecia.

Certain therapeutic agents have been known to induce hair growth in extensive areas of the trunk, limbs and even occasionally on the face. Such hair is of intermediate status in that it is coarser than vellus but not as coarse as terminal hair. The hair is generally quite short with a length of 3 cm. being about maximum. Once the patient ceases taking the drug, the hair reverts to whatever is normal for the particular site after six months to a year has elapsed. An example of such a drug is diphenylhydantoin which is an anticonvulsant drug widely used to control epileptic seizures. Hypertrichosis is frequently observed in epileptic children some two or three months after starting the drug and first becomes noticeable on the extensor aspects of the limbs and later on the trunk and face. The pattern is not unlike that sometimes caused by injury to the head. As for the hair, it is often shed when the drug is discontinued but may, in some circumstances, remain.

Streptomycin is another drug that has been found to produce hypertrichosis in much the same way as diphenylhydantoin when administered to children suffering from tuberculous meningitis. About the same effects were observed and the onset and reversal of the hypertrichosis in relation to the period of treatment with the antibiotic leave little question but that it was the causative agent.

Two treatments have been demonstrated as showing some promise in reversing male pattern alopecia. These treatments include the use of a microemulsion cream containing both estradiol and oxandrolone as its active ingredients and the use of organic silicon.

In addition to the foregoing, it has been reported in U.S. Pat. Nos. 4,139,619 and 4,968,812 that the compound minoxidil is useful for the treatment of male pattern baldness. That compound, among others, has proven to have considerable therapeutic value in the treatment of severe hypertension. It is a so-called "vasodilator" which, as the name implies, functions to dilate the peripheral vascular system. Dermatologists and others have recognized that prolonged vasodilation of certain areas of the human body other than the scalp sometimes result in increased hair growth even in the absence of any vasodilating therapeutic agent. For instance, increased hair growth around surgical scars is not uncommon. Similarly, arteriovenous fistula have been known to result in increased vascularity accompanied by enhanced hair growth. Externally-induced vasodilation of the skin, such as, for example, by repeated biting of the limbs by mental retardates and localized stimulation of the shoulders by water carries has been noted to bring on hypertrichosis in the affected areas. Be that as it may, similar techniques such as continued periodic massage of the scalp have been found totally ineffective as a means for restoring lost hair growth to the scalp. Scar tissue on the scalp inhibits rather than promotes hair growth.

The use of prostaglandins in the treatment of glaucoma has also recently been reported. Glaucoma treatments can be given by means of drugs, laser or surgery. In drug treatment, the purpose is to lower either the flow (F) or the resistance (R) which will result in a reduced intraocular pressure (IOP); alternatively to increase the flow via the uveoscieral route which also gives a reduced pressure. Cholinergic agonists, for instance pilocarpine, reduce the intraocular pressure mainly by increasing the outflow through Schlcmm's canal.

Prostaglandins, which recently have met an increasing interest as IOP-lowering substances may be active in that they will cause an increase in the uveoscleral outflow. They do not appear, however to have any effect on the formation of aqueous humor or on the conventional outflow through Schlemm's canal.

The use of prostaglandins and their derivatives is described for instance in U.S. Pat. Nos. 4.599,353 (Bito), U.S. Pat. No. 4,883,819 (Bito), U.S. Pat. No. 4,952,581 (Bito), International Application Publication No. WO89/ 03384 (Stjernschantz), European Patent Nos. 170258 (Cooper), 253094 (Goh, Yasumasa), 308135 (Ueno, Ryuzo), and by Alm, A., Surv. Ophthalmol. 41(Suppl. 2): 5105–5110 (1997); Bito, L. Z. et al., Invest. Ophthalmol. Vis. Sci. 24(3): 312–319 (1983); Camras, C. B. et al., Current Eye Res. 1(40): 205–209 (1981); Camras, C. B. et al., Invest. Ophthalmol. Vis. Sci. 28(3): 463–469 (1987); Camras, C. B. et al., Invest. Ophthalmol. Vis. Sci. 28(6): 921–926 (1987); Camras, C. B. et al., Invest. Ophthalmol. Vis. Sci. 29(9): 1428–1436 (1988); Camras, C. B. et al., Ophthalmology 103(1): 138–147 (1996); Camras, C. B. et al., Ophthalmology 103(11): 1916–1924 (1996); Giuffre, G., Graefes. Arch. Clin. Exp. Ophthalmol. 222(3): 139–141 (1985); Kaufman, P. L., Exp. Eye Res. 43(5): 819–827 (1986); Kerstetter, J. R. et al., Am. J. Ophthalmol. 105(1): 30–34 (1988); Lee, P. -Y. et al., Invest. Ophihalmol. Vis. Sci. 29(10): 1474–1477 (1988); Villumsen, J. et al., Br. J. Ophthalmol. 73(12): 975–979 (1989); and Mishima, H. K. et al., Arch. Ophthalmol. 114(8): 929–932 (1996).

U.S. Pat. Nos. 5,321,128 (Stjernschantz et al.), U.S. Pat. No. 5,422,368 (Stjernschantz et al.), U.S. Pat. No. 5,422,369 (Stjernschantz et al.), and U.S. Pat. No. 5,578,618 (Stjernschantz et al.) disclose the use of certain derivatives of prostaglandins A, E and F, in which the omega chain has been modified with the common feature of containing a ring structure, for the treatment of glaucoma or ocular hypertension. A representative prostaglandin derivative from this group, 13,14-dihydro-17-phenyl-18,19,20-trinor-PGF$_2\alpha$-isopropyl ester, also known as latanoprost or Xalatan (trade name, Pharmacia & Upjohn Company, Kalamazoo, Mich., U.S.A.), has recently been introduced into clinical use for the treatment of glaucoma. Introduction of the agent represents the culmination of years of effort by Laslo Bito and others who noted that prostaglandins may lower intraocular pressure. They continued to work with the medication prostaglandin F2 alpha (PGF$_2\alpha$) to optimize efficacy while minimizing side effects. The isopropyl ester had increased efficacy with reduced side effects thought to be partially a result of the lower dose required. Because of the troublesome persistent side effect of eye redness, or hyperemia associated with vasodilation a phenyl-substituted compound was developed. This phenyl-substituted compound was found to be effective in elimination of the troublesome clinical problem of hyperemia or vasodilation. Finally resolution of the epimeric mixture was found to be an even more potent ocular hypotensive agent. Prostaglandins represent a novel new class of drugs for the treatment of glaucoma. The agents have previously been in use in limited clinical trials to establish efficacy and safety data for FDA approval. FDA approval followed by distribution for clinical use has occurred only within the past year. Accordingly, there has not been a large clinical experience with this medication and as with other new medications unrecognized side affects are not unlikely.

U.S. Pat. No. 4,311,707 (Bernbaum et al.), U.S. Pat. No. 5,288,754 (Woodward et al.) and U.S. Pat. No. 5,532,708 (Woodward et al.) describe prostaglandin derivatives having vasodilation properties.

Finally, International Publication No. WO95/11003 (Stjernschantz et al.) discloses compositions containing prostaglandins, and derivatives and analogues thereof, particularly derivatives and analogues of prostaglandin F2α and prostaglandin E2, for increasing pigmentation of tissues or modified tissues, e.g., hair.

The foregoing notwithstanding, the literature is devoid of any suggestion that prostaglandin derivatives may be useful in the stimulation of hair growth despite extensive detailed studies of numerous patients from three disparate regions of the world (Camras, C. B. (1996a), supra; Mishima, H. K., supra; and Alm, A. and Stjernschantz, J., *Ophthalmology* 102:1243–1252 (1995)).

It is, therefore, a principal object of the present invention to provide a novel and effective treatment for the stimulation of hair growth and the treatment of male pattern baldness.

Another object of the invention forming the subject matter hereof is to provide a method of stimulating hair growth in humans and non-human animals that is compatible with various types of therapeutic agents or carriers and, therefore, would appear to be combinable with those which, by themselves, demonstrate some therapeutic activity such as, for example, microemulsion creams or topical compositions containing estradiol and oxandrolone, minoxidil or agents that block the conversion of testosterone to dihydrotesterone (Procipia).

Still another objective is the provision of a treatment for the stimulation of hair growth which, while effective for its intended purpose, is apparently non-toxic and relatively free of unwanted side effects.

An additional object of the invention herein disclosed and claimed is to provide a method for treating hair loss in men or women which can be applied by the patient under medical supervision no more stringent than that demanded for other topically-administered therapeutic agents.

Other objects of the invention are to provide a treatment for male pattern alopecia which is safe, simple, painless, cosmetic in the sense of being invisible, easy to apply and quite inexpensive when compared with hair transplants and the like.

SUMMARY OF THE INVENTION

This invention provides pharmaceutical compositions for topical application comprising a prostaglandin compound, in free form or a pharmaceutically acceptable salt thereof, in association with a pharmaceutical carrier adapted for topical application to mammalian skin. Preferably, the prostaglandin compound is a $PGF_2\alpha$ derivative, such as 13,14-dihydro-15-dehydro-17-phenyl-18,19,20-trinor-$PGF_2\alpha$ or a pharmaceutically acceptable salt thereof.

Another aspect of the invention provides methods for stimulating the rate of hair growth and for stimulating the conversion of vellus hair or intermediate hair to growth as terminal hair in a human or non-human animal by administering to the skin of the animal an effective amount of a prostaglandin PGA, PBE or PGF compound wherein the alpha chain of the compound has the formula:

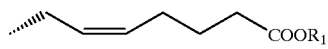

in which $R_1$ is H or an alkyl group having 1–10 carbon atoms, especially 1–6 atoms, for instance methyl, ethyl, propyl, isopropyl, butyl, isobutyl, neopentyl or benzyl or a derivative giving the final substance equivalent properties as a hair growth stimulating agent; and the omega chain of the compound has the formula:

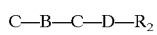

wherein C is a carbon atom or loweralkyl chain, optionally substituted with one or more —OH groups;

B is a single bond, a double bond or a triple bond;

D is a chain with 1–10 carbon atoms, optionally substituted with one or more —OH groups; and $R_2$ is H or a phenyl group which is unsubstituted or has one or more substituents selected from the group consisting of $C_1$–$C_5$ alkyl groups, $C_1$–$C_4$ alkoxy groups, trifluoromethyl groups, $C_1$–$C_3$ aliphatic acylamino groups, nitro groups, halogen atoms, and phenyl groups; or an aromatic heterocyclic group having 5–6 ring atoms, like thiazol, imidazole, pyrrolidine, thiopene and oxazole; or a cycloalkane or a cycloalkene with 3–7 carbon atoms in the ring, optionally substituted with lower alkyl groups with 1–5 carbon atoms;

and the pharmacologically acceptable acid addition salts thereof, in association with a topical pharmaceutical carrier.

These and other aspects of the invention will become apparent from the description of the invention which follows below.

DETAILED DESCRIPTION OF THE PREFERRED EMBODIMENT

Alopecia (baldness) a deficiency of either normal or abnormal hair, is primarily a cosmetic problem in humans. It is a deficiency of terminal hair, the broad diameter, colored hair that is readily seen. However, in the so-called bald person although there is a noticeable absence of terminal hair, the skin does contain vellus hair which is a fine colorless hair which may require microscopic examination to determine its presence. This vellus hair is a precursor to terminal hair. In accordance with the invention as described herein, prostaglandin derivatives and analogues can be used to stimulate, such as stimulating the conversion of vellus hair to growth as terminal hair as well as increasing the rate of growth of terminal hair.

In the course of treating patients having glaucoma, treatment may only be appropriate in one eye. Within the course of daily practice it was discovered that a patient who had taken a representative prostaglandin derivative, latanoprost, for 17 weeks has lashes that were longer, thicker and fuller in the treated eye than in the non-treated eye. On examination the difference was found to be very striking. The lashes were about 30% longer and had a more full dense appearance in the treated eye. The lash appearance on the lids of the treated eye would have appeared quite attractive if it represented a bilateral phenomenon. Because of its asymmetric nature, the long lashes on one side could be construed as disturbing from a cosmetic standpoint. Because of the very unusual appearance a systematic examination of other patients who were taking latanoprost in only one eye was made. It soon became apparent that this altered appearance was not an isolated finding. Comparison of the lids of patients who were taking latanoprost in only one eye following 5–6 weeks of use revealed subtle changes in the lashes and adjacent hairs of the latanoprost-treated side in several patients. Definite differences could be identified to varying degrees in the lashes and adjacent hairs of all patients who were taking the drug on a unilateral basis for longer than 3 months.

These findings were totally unexpected and surprising. Minoxidil is thought to stimulate hair growth by its ability to cause vasodilation suggesting that agents with such a capability may be uniquely effective in stimulating hair growth. The finding that prostaglandin derivatives, such as latanoprost, stimulate hair growth is especially surprising and unexpected since latanoprost was specifically tailored to eliminate clinical hyperemia and vasodilation.

The changes in the lashes were apparent on gross inspection in several patients once attention was focused on the issue. In those with light colored hair and lashes, the differences were only seen easily with the aid of the high magnification and lighting capabilities of the slit lamp biomicroscope. In the course of a glaucoma follow up examination, attention is generally immediately focused on the eye itself. Because of the high power magnification needed only one eye is seen at a time and the eye is seen at a high enough power that the lashes are not in focus. At these higher powers, any lash asymmetry between the two eyes is not likely to be noticed except by careful systematic comparison of the lashes and adjacent hairs of the eyelids of the two eyes.

Observed parameters leading to the conclusion that more robust hair growth occurred in the treated area following administration of latanoprost were multiple. They included increased length of lashes, increased numbers of lashes along the normal lash line, increased thickness and luster of lashes, increased auxiliary lash-like terminal hair in transitional areas adjacent to areas of normal lash growth, increased lash-like terminal hairs at the medial and lateral canthal area, increased pigmentation of the lashes, increased numbers, increased length, as well as increased luster, and thickness of fine hair on the skin of the adjacent lid, and finally increased perpendicular angulation of lashes and lash-like terminal hairs. The conclusion that hair growth is stimulated by latanoprost is thus supported not by evidence of a difference in a single parameter but is based on multiple parameters of hair appearance in treated vs. control areas in 43 subjects. This finding is entirely unexpected and represents a previously unrecognized effect of prostaglandins on stimulation of hair follicles. Increased pigmentation of the iris, primarily those with hazel and light brown eyes is, however, a known side effect of latanoprost and was reported to the FDA during clinical trials because of a concern that some patients might find a change in iris color unacceptable, especially if unilateral. The change in pigmentation of the iris is thought to result from stimulation of melanin production, rather than proliferation of melanocytes. Another manifestation of the ability of the drug latanoprost to alter melanin production appears to be an analogous stimulation of melanin production in the hair follicles. The increased pigmentation observed may not be limited to selective stimulation of melanin production. In view of all the other evidence of increased activity of the hair follicles described in this patent it seems likely that the increased pigmentation is a manifestation of a much broader robust stimulation of all the components involved in growth and development of the hair within the hair follicle. Thus, described herein is the stimulation of growth of hairs of different types in different areas, the lashes, transitional auxiliary hairs adjacent to the lashes and fine microscopic hair on the skin. The modified hairs of the lashes normally turn over slowly and are in their resting phase longer than hair on, for example, the scalp. The ability to cause differences in appearance of lashes, the ability to stimulate conversion of vellus or intermediate hair to terminal hairs in transitional areas and the ability to stimulate growth of vellus hair on the skin indicates that the agent is a diversely effective and efficacious agent for the stimulation of hair growth. Thus, the present invention provides a treatment by prostaglandins of hair of the scalp, eyebrows, beard and other areas that contain hair that results in increased hair growth in the corresponding areas.

Patients that are treated in or around the eye with compounds of the invention, such as latanoprost regularly develop hypertrichosis including altered differentiation, numbers, length, thickness, curvature and pigmentation in the region of treatment. The phases of the hair cycle require coordinated control of cellular proliferation, differentiation, migration, angiogenesis, involution and apoptosis. Numerous cellular interactions occur and require simultaneous participation of epithelial cells, dermal papilla fibroblasts, nerve fibers, melanocytes, and vascular endothelial cells.

Although practice of the invention is not limited to any particular mechanism of operation, a review of properties characterized through laboratory studies provide several possible mechanisms that may individually or in concert explain the altered growth pattern of hair follicles observed in the current clinical study. Hair follicles have a rich vasculature in the region of the base of the hair bulb. PGF2 alpha analogs can cause a vasodilation effect and through that mechanism may provide enhanced perfusion to the region of the hair bulb and thus stimulate increased trophic activity in the hair follicles.

PGF2 alpha analogues stimulate cell surface receptors linked by a G protein to phosphoralase C, an enzyme with the principle property of triggering the activation of a family of protein kinases. The protein kinases produce a varied array of responses that play a key role in trophic metabolic activity and are of fundamental importance in cell growth (Darnell, J. et al., *Molecular Cell Biology* (Darnell, J., Lidish, H., Baltimore, D., Eds.), W. H. Freeman and Company, New York, N.Y., pp. 738–743 (1990)).

Modulation of the extracellular matrix environment and integrins, another well characterized property of PGF2 alpha analogues alters tensegrity. Tensegrity represents an architectual system in which structures stabilize themselves by balancing the counteracting forces of compression and tension to give shape and structure to natural and artificial forms. The cytoskeleton of the living cell is a framework composed of compressive "girders" inside the cell that are represented either by microtubules or large bundles of cross-linked microfilaments with the cytoskeleton. A third component of the cytoskeleton, the intermediate filaments, are the integrators connecting microtubules and contratile microfilaments to one another as well as to the cell surface membrane and to the cell's nucleus. The intermediate filaments act as guy wires, stiffening the central nucleus and securing it in place. By modifying the shape of the cell as occurs with alterations in the extracellular matrix researchers can switch the cells between different genetic programs. For example, by altering the extracellular environment they can cause the cells to divide, to differentiate, to remain in steady state, or to involute or to activate a death program known as apoptosis. Alterations in the extracellular matrix can thus evoke responses such as gene expression, cell division and prevention of apoptosis (Darnell, J. et al., supra), and prolong the hair cycle. By increasing the duration of the cell cycle, the interval in the anagen phase may be increased permitting hypertrophy of the follicles with longer and thicker hairs as observed. PGF2 alpha is capable of direct induction of DNA replication and stimulates cell division and growth in a number of tissues in vitro (Fagot, D. et al., *Endocrinology* 132:1724–1734 (1993).

Latanoprost, an analogue of PGF2 alpha, retains the well-characterized functional groups that confer the ability to act as a mitogen or growth factor (Jimenez de Asua, L. et al., *Journal of Biological Chemistry* 256:8774–8780 (1983).

Properties characterized through laboratory studies thus provide several possible mechanisms that may individually or in concert explain the altered growth pattern of hair follicles observed in the current clinical study.

Prostaglandin derivatives have the general structure:

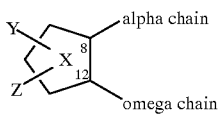

wherein X represents the alicyclic ring $C_8$–$C_{12}$ which may contain one or more double bonds, Y and Z represent substituents in the 9, 10 and/or 11 positions that may be hydrogen, hydroxyl or oxo—in either stereochemical configuration, and the bonds between the ring and the side chains represent the various isomers. The prostaglandins PGA, PGB, PGC, PGD, PGE, PGF and PGJ X have the following ring X structural formulas:

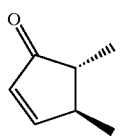

PGA

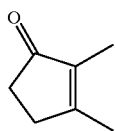

PGB

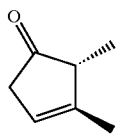

PGC

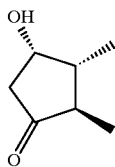

PGD

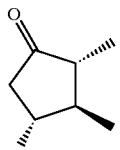

PGE

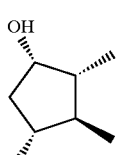

PGF

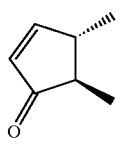

PGJ

Particularly useful in the practice of the present invention are derivatives of the prostaglandins characterized by presence or lack of modifications to their omega chain and the presence or lack of various modifications of the alpha chain.

The alpha chain can typically be the naturally occurring alpha chain, which is esterified to the structure:

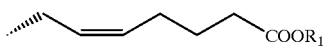

in which $R_1$ is H or an alkyl group, preferably with from 1 to 10 carbon atoms, especially 1 to 6 atoms, for instance methyl, ethyl, propyl, isopropyl, butyl, isobutyl, neopentyl or benzyl or a derivative giving the final substance equivalent properties as a hair growth stimulating agent. The chain could preferably be a $C_6$–$C_{10}$ chain which can be saturated or unsaturated, having one or more double bonds, and allenes or a triple bond. In addition, the chain can contain one or more substituents such as alkyl groups, alicyclic rings, or aromatic rings with or without hetero atoms.

The omega chain is defined by the following formula:

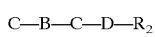

wherein C is a carbon atom or loweralkyl chain, optionally substituted with one or more —OH groups;

B is a single bond, a double bond or a triple bond;

D is a chain with from 1 to 10 carbon atoms, preferably more than 2 and less than 8 atoms, and especially less than 5 atoms, optionally substituted with one or more —OH groups. Presently preferred derivatives have a chain with 3 atoms. The chain is optionally interrupted by preferably not more than two hetero atoms (O, S, or N), and may optionally be substituted with the substituents on each carbon atom of the chain being H, alkyl groups, preferably lower alkyl groups with 1–5 carbon atoms, a carbonyl group, or a hydroxyl group, whereby the substituent on $C_{15}$ preferably being a carbonyl group, or (R)—OH or (S)—OH, each chain D containing preferably not more than three hydroxyl groups or more than three carbonyl groups;

$R_2$ is H or a ring structure such as a phenyl group which is unsubstituted or has one or more substituents selected from $C_1$–$C_5$ alkyl groups, $C_1$–$C_5$ haloalkyl groups such as trifluoromethyl groups, $C_1$–$C_4$ alkoxy groups, $C_1$–$C_4$ haloalkoxy groups such as trifluoromethoxy groups, $C_1$–$C_3$ aliphatic acylamino groups, nitro groups, halogen atoms such as fluoro or chloro, and an phenyl group; or an aromatic heterocyclic group having 5–6 ring atoms, like thiazol, imidazole, pyrrolidine, thiopene and oxazole; or a cycloalkane or a cycloalkene with 3–7 carbon atoms in the ring, optionally substituted with lower alkyl groups withal-5 carbon atoms.

Some examples of representative derivatives useful in the practice of the invention having a phenyl substituent on the omega chain include the compounds shown in Table 1:

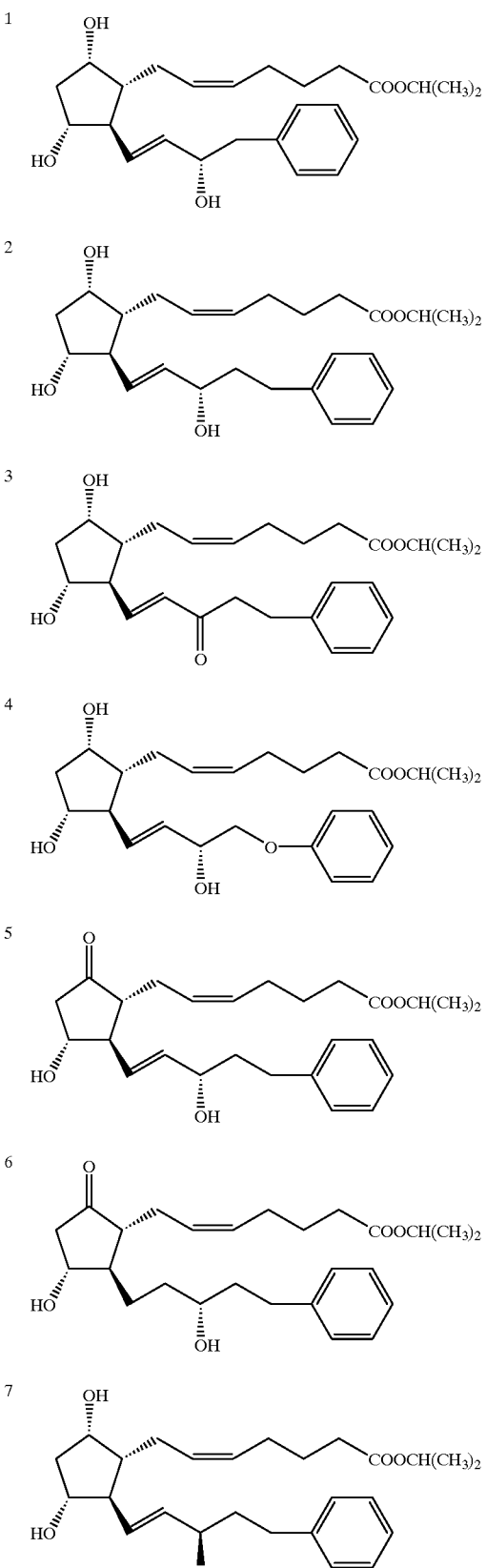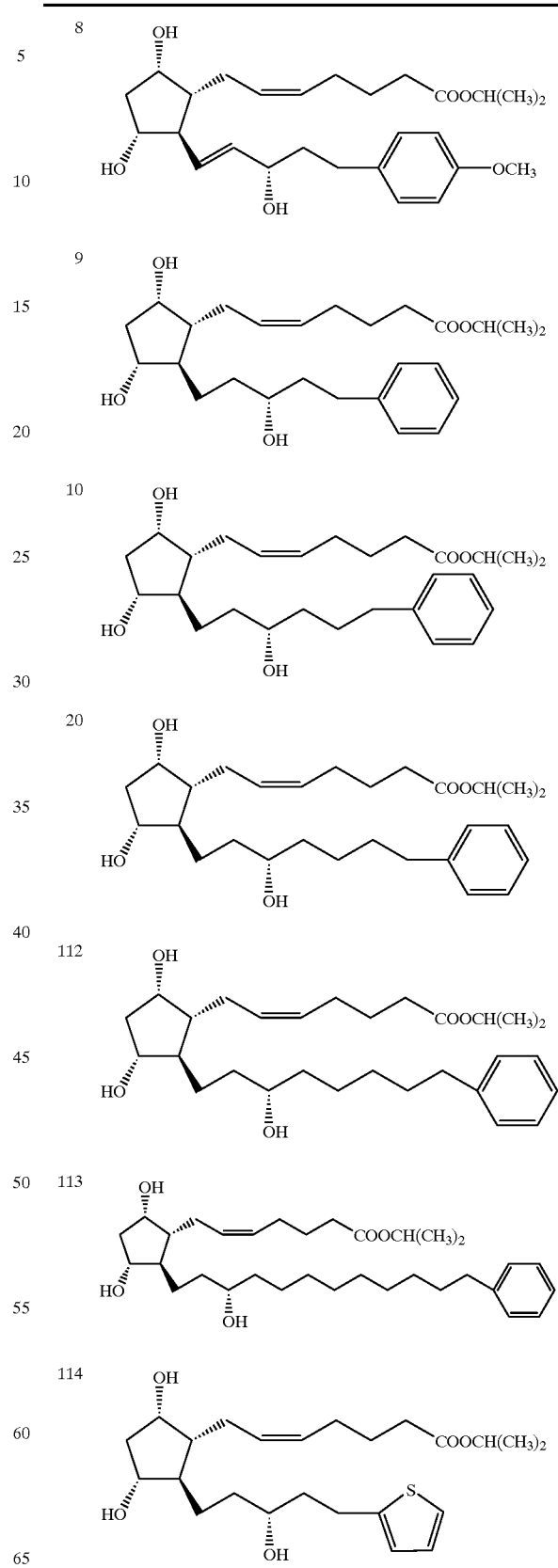

TABLE 1-continued
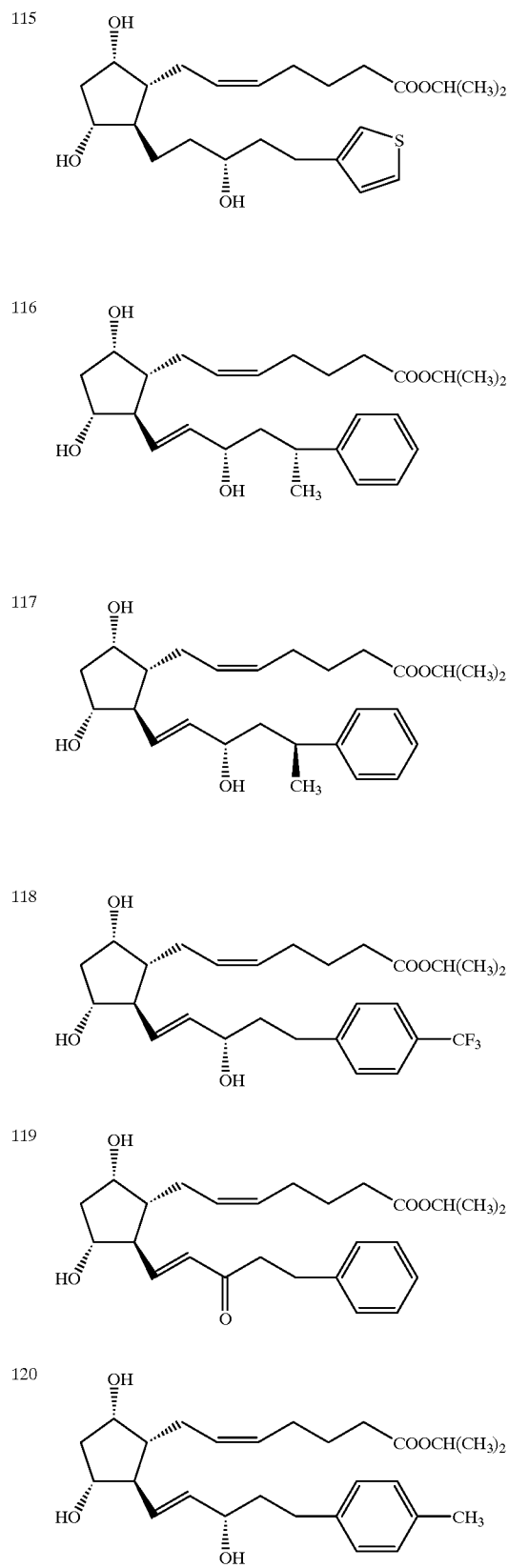
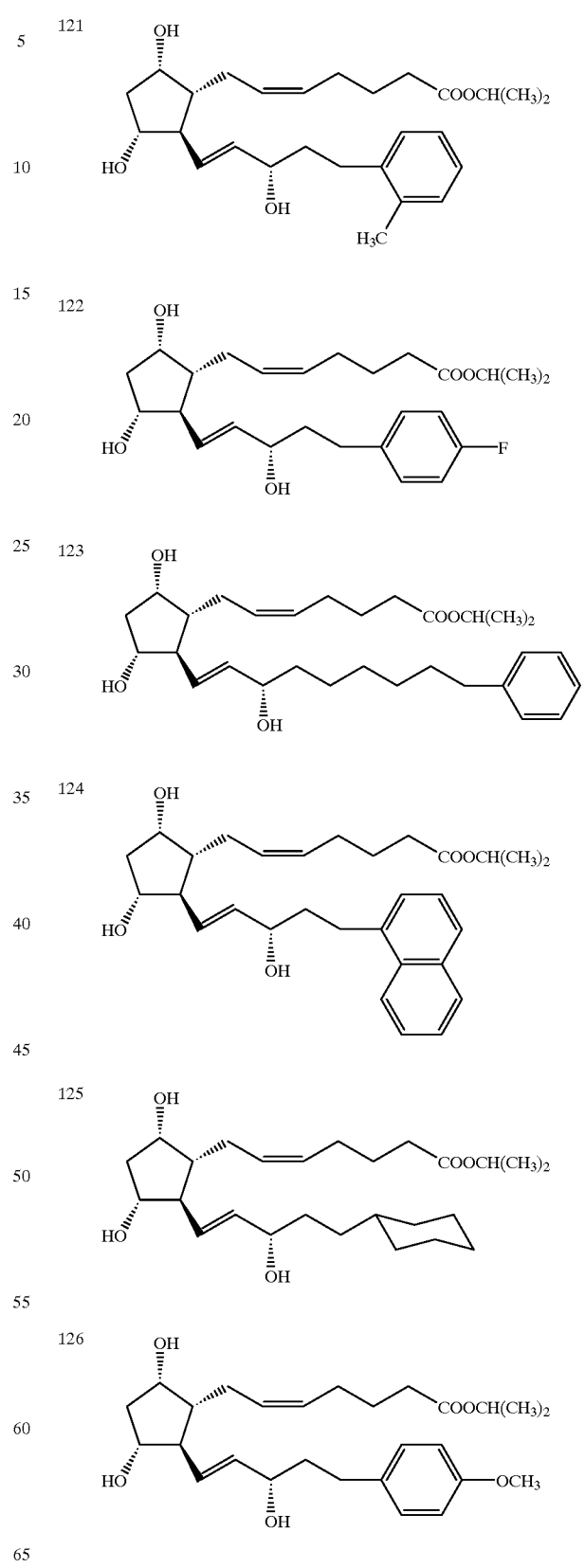

TABLE 1-continued

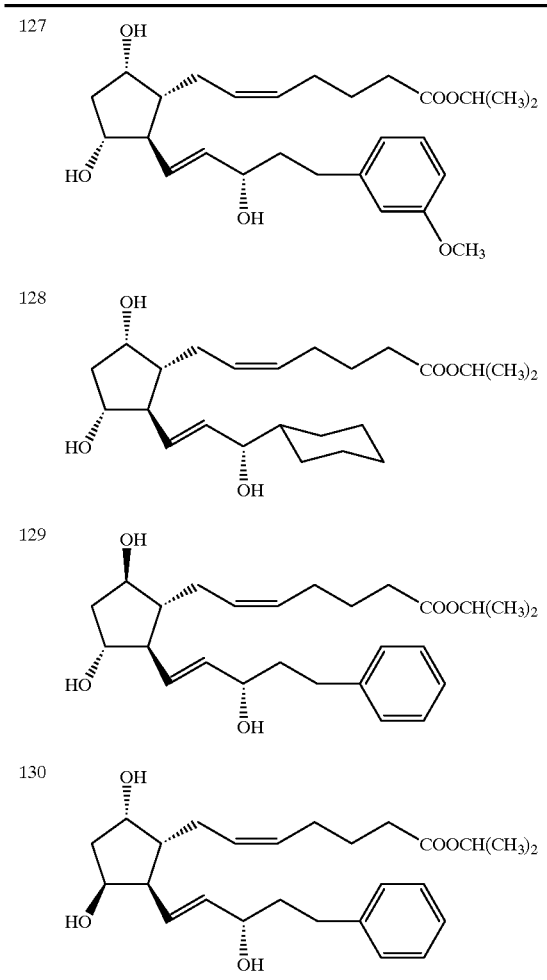

In Table 1, the structures have the following nomenclature, as used herein:
(1) 16-phenyl-17,18,19,20-tetranor-PGF$_2$α-isopropyl ester
(2) 17-phenyl-18,19,20-trinor-GF$_2$α-isopropyl ester
(3) 15-dehydro-17-phenyl-t8,19,20-PGF$_2$α-isopropyl ester
(4) 16-phenoxy-17,18,19,20-trinor-PGF$_2$α-isopropyl ester
(5) 17-phenyl-18,19,20-trinor-PGE$_2$α-isopropyl ester
(6) 13,14-dihydro-17-phenyl-18,19,20-trinor-PGA$_2$α-isopropyl ester
(7) 15-(R)-17-phenyl-18,19,20-trinor-PGF$_2$α-isopropyl ester
(8) 16-[4-methoxyphenyl]-17,18,19,20-tetranor-PGF$_2$α-isopropyl ester
(9) 13,14-dihydro-17-phenyl-18,19,20-trinor-PGF$_2$α-isopropyl ester
(10) 18-Phenyl-19,20-dinor-PGF$_2$α-isopropyl ester
(20) 19-phenyl-20-nor-PGF$_2$α-isopropyl ester
(112) 20-phenyl-PGF$_2$α-isopropyl ester
(113) 20-(4-phenylbutyl)-PGF$_2$α-isopropyl ester
(114) 17-(2-thiophene)-18,19,20-trinor-PGF$_2$α-isopropyl ester
(115) 17-(3-thiophene)-18,19,20-trinor-PGF$_2$α-isopropyl ester
(116 and 117) 17-R,S-methyl-17-phenyl-18,19,20-trinor-PGF$_2$α-isopropyl ester
(118) 17-(4-trifluoromethyl phenyl)-18,19,20-trinor-PGF$_2$α-isopropyl ester
(119) 13,14-dihydro-15-dehydro-17-phenyl-18,19,20-trinor-PGF$_2$α-isopropyl ester
(120) 17-(4-methylphenyl)-18,19,20-trinor-PGF$_2$α-isopropyl ester
(121) 17-(2-methylphenyl)-18,19,20-trinor-PGF$_2$α-isopropyl ester
(122) 17-(4-fluorophenyl)-18,19,20-trinor-PGF$_2$α-isopropyl ester
(123) 20-(methylenephenyl)-PGF$_2$α-isopropyl ester
(124) 17-naphthyl-18,19,20-trinor-PGF$_2$α-isopropyl ester
(125) 17-cyclohexyl-18,19,20-trinor-PGF$_2$α-isopropyl ester
(126) 17-(4-methoxyphenyl)-18,19,20-trinor-PGF$_2$α-isopropyl ester
(127) 17-(3-methoxyphenyl)-18,19,20-trinor-PGF$_2$α-isopropyl ester
(128) 15-cyclohexyl-16,17,18,19,20-pentanor-PGF$_2$α-isopropylester The synthesis of the isopropyl esters described above has been disclosed in U.S. Pat. Nos. 5,321,128, 5,422,368, 5,422,369, and 5,578,618, but any alkyl ester of the prostaglandin derivatives, preferably with 1–10 carbon atoms and especially with 1–6 atoms, for instance methyl, ethyl, propyl, isopropyl, butyl, isobutyl, neopentyl or benzyl esters, may be used in the practice of the invention.

Also preferred prostaglandin derivatives at present are those in which the omega chain of the prostaglandin has the 18,19,20-trinor form and especially the 17-phenyl analogues, such as the 15-(R)-, 15-dehydro and 13,14-dihydro-17-phenyl-18,19,20-trinor forms, and the carboxylic acid esters thereof. Such derivatives are represented by (3), (6), (7) and (9) in the formulas given in Table 1.

Also preferred derivatives include those in which the omega chain has not been substituted with a phenyl ring structure, such as those compounds described in U.S. Pat. Nos. 4,311,707, 5,288,754 and 5,352,708.

In the formula given above the presently preferred prostaglandin derivatives are obtained when the prostaglandin is a derivative of PGA$_2$, PGE$_2$, and PGF$_2$α, where:

B is a single bond or a double bond,

D is a carbon chain with 2–5, especially 3 atoms; C$_{15}$ having a carbonyl or (S)—OH substituent and C$_{16}$–C$_{19}$ having lower alkyl substituents, or preferably H, R$_2$ is H or a phenyl ring, optionally having substituents selected among alkyl and alkyoxy groups.

One presently preferred compound for use in the practice of the present invention is 13,14-dihydro-15-dehydro-17-phenyl-18,19,20-trinor-PGF$_2$α isopropyl ester, also known as latanoprost and sold under the name Xalatan by Pharmacia & Upjohn Company, Kalamazoo, Mich., U.S.A. This compound has the following structure:

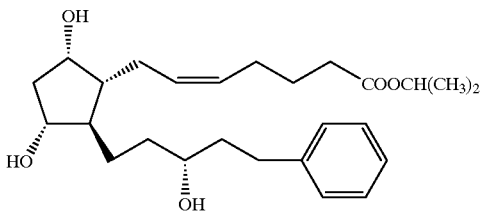

The invention thus relates to the use of certain derivatives of $PGA_2$, $PGE_2$ and $PGF_2\alpha$, or prodrugs of the active compounds, for treatment for the stimulation of hair growth. As used herein, hair growth includes hair associated with the scalp, eyebrows, eyelids, beard, and other areas of the skin of animals. Among the derivatives defined above, some may be irritating or otherwise not optimal, and in certain cases not even useful due to adverse effects and these are excluded in that the group of prostaglandin derivatives defined above is limited to therapeutically effective, that is hair growth stimulating, and physiologically acceptable derivatives. So, for instance, while compound (1) above (16-phenyl-17,18, 19,20-tetranor-$PGF_2\alpha$-isopropyl ester, Table 1) may be irritating, the irritation may be reduced or eliminated by substituting the phenyl ring with a methoxy group giving compound (8), Table 1, which represents a therapeutically more useful compound. On the other hand, other preferred groups are not substituted with a ring structure, which creates a greater degree of hyperemia (vasodilation) of the treated tissues.

In accordance with one aspect of the invention, the prostaglandin derivative is mixed with a dermatologically compatible vehicle or carrier known per se. The vehicle which may be employed for preparing compositions of this invention may comprise, for example, aqueous solutions such as e.g., physiological salines, oil solutions or ointments. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity. Furthermore, it is also possible to use soluble or insoluble drug inserts when the drug is to be administered.

The invention is also related to dermatological compositions for topical treatment for the stimulation of hair growth which comprise an effective hair growth stimulating amount of one or more prostaglandin derivatives as defined above and a dermatologically compatible carrier. Effective amounts of the active derivatives will vary depending on the derivative employed, frequency of application and desired result, but will generally range from about 0.0000001 to about 50% by weight of the dermatological composition. Representative compositions may thus comprise from about 0.001 to about 50 μg of the derivatives in about 1 to about 100 μg of total dermatological composition, more preferably from about 0.1 to about 30 μg in about 10 to about 50 μg of the composition.

The present invention finds application in all mammalian species, including both humans and animals. In humans, the compounds of the subject invention can be applied for example, to the scalp, face, beard, head, pubic area, upper lip, eyebrows, and eyelids. In animals raised for their pelts, e.g., mink, the compounds can be applied over the entire surface of the body to improve the overall pelt for commercial reasons. The process can also be used for cosmetic reasons in animals, e.g., applied to the skin of dogs and cats having bald patches due to mange or other diseases causing a degree of alopecia.

The pharmaceutical compositions contemplated by this invention include pharmaceutical compositions suited for topical and local action.

The term "topical" as employed herein relates to the use of a prostaglandin compound, derivative or analogue as described herein, incorporated in a suitable pharmaceutical carrier, and applied at the site of thinning hair or baldness for exertion of local action. Accordingly, such topical compositions including those pharmaceutical forms in which the compound is applied externally by direct contact with the skin surface to be treated. Conventional pharmaceutical forms for this purpose include ointments, liniments, creams, shampoos, lotions, pastes, jellies, sprays, aerosols, and the like, and may be applied in patches or impregnated dressings depending on the part of the body to be treated. The term "ointment" embraces formulations (including creams) having oleaginous, absorption, water-soluble and emulsion-type bases, e.g., petrolatum, lanolin, polyethylene glycols, as well as mixtures of these.

Although the invention is not limited to any particular mechanism or theory of action, various physiological considerations are relevant to the concepts disclosed herein. When hair follicles initially form embryologically, they do so by means of a stimulus sent from a group of specialized fibroblast cells in the dermis which will become the dermal papilla. These dermal papilla cells induce cells of the epidermis to migrate downward and ultimately form the hair follcile. At each hair cycle, the epithelial elements and dermal papilla migrate upward within the skin to an area close to the surface and undergo a programmed involution or dedifferentiation. Throughout life each new hair cycle recapitulates the embryologic event by repeatedly transitioning from the resting telogen or involutional stage beneath the surface of the skin to the anagen phase with associated proliferation, differentiation and migration of epithelial elements in response to induction by stimulus factors in the dermal papilla.

The prostaglandin derivatives of the invention, such as PGF2 alpha analogs, are local hormones or paracrine agents that induce local effects in cells in their immediate area. The cells are also capable of autocrine signalling, thus, they can also send signals to themselves by binding back to their own receptors. During development, for example, once a cell has been directed into a particular path of differentiation, it may begin to secrete autocrine signals that reinforce this developmental decision.

Because autocrine signaling is most effective when carried out simultaneously by neighboring cells of the same type, it may be used to encourage groups of identical cells to make the same developmental decisons. For this reason, autocrine signalling is thought to be one possible mechanism underlying the "community effect" observed in early development, where a group of identical cells can respond to a differentiation inducing signal but a single isolated cell of the same type cannot. These signalling mechanisms provide a reinforcing or amplifying effect. Paracrine and autocrine signalling are not confined to development, however, and the eiconsanoids are signalling molecules that regularly act on mature systems.

The unique observations described herein indicate that PGF2 alpha analogs may be able to initiate hair growth in response to very low total dosages and very short dosage durations. In view of the recapitulation of embryologic behavior at the initiation of the hair cycle it might be anticipated that very small dosages at a critical time in the resting or telogen stage may be able to initiate the anagen phase of growth by inducing folicles to trigger the anagen phase and then sending autocrine signals that reinforce and amplify that developmental decision to differentiate into a mature follicle. PFG2 alpha analogues, rather than reaching a level where increased dosage will simply not cause an increased effect may, rather, cause a decrease in the effectiveness of the agent. For example, this has been shown to be true of the prostaglandin derivative latanoprost in relation to its effect on intraocular pressure where higher dosages may not provide as effective a pressure lowering response.

For the reasons mentioned above, one presently preferred embodiment of the invention comprises treating a human or non-human animal with relatively low doses of a prostaglandin of the invention that will deliver a dosage found in the Examples or as little as 0.1 nanograms (ng), depending on the analogue and mode of application.

Typically, the prostaglandins are applied repeatedly for a sustained period of time topically on the part of the body to be treated, for example, the eyelids, eyebrows, skin or scalp. The preferred dosage regimen will generally involve regular, such as daily, administration for a period of treatment of at least one month, more preferably at least three months, and most preferably at least six months.

Alternatively, the prostaglandins may be applied intermittently, or in a pulsed manner. For example, in the studies described in Example 1, supra, in each of the patients who took the drug for a duration of 5 days, effects were present that persisted for as long as 14 months. In contrast, several patients who used the drug for 4 months or more on a sustained chronic basis had a loss of the effect within 4 months of stopping the drug. Accordingly, it is a presently preferred alternative embodiment of the invention to apply the prostaglandins on an intermittent or pulsed dosage schedule. For example, the prostaglandins of the invention may be used for two or more days, stopped, then restarted again at a time from between 2 weeks to 3 months later in the case of eyelashes, and at even more long-spaced intervals in the case of the scalp.

This pulsed delivery approach may be used by itself or with other agents that may set the stage for initiation and perpetuation of the anagen phase of hair growth. For example, agents such as estrogen creams may at times make the follicle more responsive to the inductive and differentiating influences of eiconsonoids. Alternatively, the pulsed approach may be used with agents such as the alpha reductase drugs, such as, for example, proscar or Procipia. An additional alternative is the use in a pulsed fashion with minoxidil.

For topical use on the eyelids or eyebrows, the active prostaglandins as well as their derivatives and analogues, including esters and salts, can be formulated in aqueous solutions, creams, ointments or oils exhibiting physiologically acceptable osmolarity by addition of pharmacologically acceptable buffers and salts. Such formulations may or may not, depending on the dispenser, contain preservatives such as benzalkonium chloride, chlorhexidine, chlorobutanol, parahydroxybenzoic acids and phenylmercuric salts such as nitrate, chloride, acetate, and borate, or antioxidants, as well as additives like EDTA, sorbitol, boric acid etc. as additives. Furthermore, particularly aqueous solutions may contain viscosity increasing agents such as polysaccharides, e.g., methylcellulose, mucopolysaccharides, e.g., hyaluronic acid and chondroitin sulfate, or polyalcohol, e.g., polyvinylalcohol. Various slow releasing gels and matrices may also be employed as well as soluble and insoluble ocular inserts, for instance, based on substances forming in-situ gels. Depending on the actual formulation and prostaglandin analogue to be used, various amounts of the drug and different dose regimens may be employed. Typically, the daily amount of prostaglandin for treatment of the eyelid may be about 0.1 ng to about 100 mg per eyelid, more preferably about 1 ng to about 100 $\mu$g per eyelid.

For topical use on the skin and the scalp, the prostaglandin can be advantageously formulated using ointments, creams, liniments or patches as a carrier of the active ingredient. Also, these formulations may or may not contain preservatives, depending on the dispenser and nature of use. Such preservatives include those mentioned above, and methyl-, propyl-, or butyl-parahydroxybenzoic acid, betain, chlorhexidine, benzalkonium chloride, and the like. Various matrices for slow release delivery may also be used. Typically, the dose to be applied on the scalp is in the range of about 0.1 ng to about 100 mg per day, more preferably about 1 ng to about 10 mg per day, and most preferably about 10 ng to about 1 mg per day depending on the prostaglandin and the formulation. To achieve the daily amount of medication depending on the formulation, the prostaglandin may be administered once or several times daily with or without antioxidants.

Several different prostaglandins may be employed to achieve the therapeutic effect on stimulation of hair growth in the types of tissues discussed above, e.g., the eyelid, eyebrow, scalp and skin. Particularly preferred prostaglandins are those of the A, F and E types. To minimize side effects, such as irritation and redness of the skin, it may be advantageous to use prostaglandin derivatives or analogues which have been found to exert less side effects, such as phenyl- and other ring-substituted prostaglandin derivatives. On the other hand, increased hyperemia experienced with other substituents may be more beneficial in causing increased vasodilation, resulting in hair growth. Prostaglandin derivatives that exhibit high pharmacological activity and no or only very small side effects, such as 13,14-dihydro-15-dehydro-17-phenyl-18,19,20-trinor-PGF$_2\alpha$ and its carboxylic acid esters, are also presently particularly preferred, especially in use in large areas of the skin or scalp.

EXAMPLES

Example 1

In Vivo Treatment

A study was initiated to systematically evaluate the appearance of lashes and hair around the eyes of patients who were administering latanoprost in only one eye. The study involved 10 Caucasian subjects, 5 male, 5 female, average age 71±13 years, (ranging from 48–94 years). All patients had glaucoma. Each subject was treated daily by the topical application of one drop of 13,14-dihydro-17-phenyl-18,19,20-trinor-PGF$_2\alpha$-isopropyl ester (latanoprost) at a dosage of 1.5 $\mu$g/ml/eye/day (0.005% ophthalmic solution, sold under the name Xalatan by Pharmacia & Upjohn Company, Kalamazoo, Mich., U.S.A.) to the region of one eye by instilling the drop onto the surface of the eye. The region of the fellow control eye was not treated with latanoprost and served as a control.

In the course of treatment with eye drops, there is typically spontaneous tearing, and excess fluid from the drops and associated tears gathers at the lid margins. In the course of wiping the drug containing fluid from the lid margins and adjacent lid, a thin film of the fluid is routinely spread to contact the adjacent skin of the lid area. This widespread exposure of the skin around the lid to the effect of drops is regularly demonstrated in patients who develop a contact dermatitis. Typically the entire area of the upper and lower lid are involved with induration, erythema and edema demonstrating the regular extensive exposure of the ocular adnexa to the influence of topically applied drugs.

The study was limited to subjects who had administered latanoprost to one eye for more than 3 months. The mean duration of exposure to latanoprost prior to assessing the parameter of lash growth between the control and study eye was 129 days (range 90–254 days). Observations were made under high magnification at the slit lamp biomicroscope. Documentation of differences between the control and treatment areas was accomplished using a camera specially adapted for use with the slit lamp biomicroscope. Photographs are on file documenting each of the observations described below.

The results of the observations are as follows:

Length of lashes: Increased length of eyelashes was regularly observed on the side treated with latanoprost. The difference in length varied from approximately 10% to as much as 30%.

Number of lashes: Increased numbers of lashes were observed in the treated eye of each patient. In areas where there were a large number of lashes in the control eye, the increased number of lashes in the latanoprost-treated eye gave the lashes on the treated side a more thickly matted overall appearance. The difference in lash numbers was most easily appreciated in the area of the lower lid. Lashes of the lower lid were typically relatively sparse in the control eye. The lower lid of the treated eye consistently had more lashes. Portions of the lateral part of the lower lid in some patients had either extremely sparse or absent lashes in the control eye, the same lid area of the treated eye generally had an apparent full complement of lashes creating an appearance of a lash distribution and density more like that seen in the central portion of the lower lid.

Pigmentation: Lash pigmentation was increased in the treated eye of most patients. The difference was subtle in eyes of patients with gray or blonde colored hair. Increased pigmentation was more prominent in lashes and adjacent hairs of patients who had brown or black hair.

Increased luster, brilliance and sheen: The lashes of the treated eye had the appearance of an increased luster, which may be variously described as increased sheen, brilliance, gloss, glow, polish, shine or patina compared to the control eye. This difference in appearance was present in patients ranging from those with light blond hair to those with black hair. This increased luster, sheen or brilliance was in addition to, and appeared to be independent of, the appearance of increased pigmentation that was observed in some patients with darker hair and lashes.

Auxiliary lash-like hair growth: Several patients had an apparent increase in lash-like hair in transitional areas adjacent to areas of normal lash distribution. These prominent robust appearing lash-like hairs appeared to be of comparable length to the actual lashes. These long, thick lash-like hairs were present in the central portion of the lids of several patients in a linear arrangement just above the lash line. Hairs were present at similar locations in the control eyes but were by contrast thinner or more fine in appearance, had less luster and pigment and were more flat against the skin of the lid typical of vellus or intermediate hairs. In several patients, lash-like terminal hairs were growing luxuriantly in the medial canthal area in the treated eye. In the corresponding control eye, vellus hairs were seen at the same location. Lash-like hairs were also present in the lateral canthal area of the treated eye but not the control eye in several subjects. Large lashes are not normally present at the lateral canthus and the area is generally free of all but a few occasional very fine lashes or vellus hairs. Growth of lashes directly from the lateral canthus can create a medical problem. Because of the anatomic arrangement, dense lash growth directly from the lateral canthus can result in lashes growing directly toward the eye, causing an irritation of the eye tissue.

Increased growth of vellus hair on lids: Fine microscopic vellus hair is present on the skin of the lids and is easily seen with the slit lamp biomicroscope. This vellus hair is typically denser adjacent to and below the lateral portion of the lower lids. While remaining microscopic, vellus hairs were increased in number, appeared more robust and were much longer and thicker in treated than in control eyes in the areas below and lateral to the lower lid.

Perpendicular angulation of hairs: In areas where there were lash-like hairs above the lash line and in the medial and lateral canthal areas, the hairs were much longer, thicker and heavier. They also left the surface of the skin at a more acute angle, as though they were stiffer or held in a more erect position by more robust follicles. This greater incline, pitch, rise or perpendicular angulation from the skin surface gave the appearance of greater density of the hairs.

The foregoing observations clearly establish that an autocoid, more specifically, a prostaglandin derivative (latanoprost) can be used to increase the growth of hair in man. This conclusion is based on the regular and consistent finding of manifestations of increased hair growth in treated vs. control areas in human subjects. The conclusion that the drug latanoprost is capable of inducing increased robust growth of hair is based not on a single parameter, i.e., length, but is based on multiple lines of evidence as described in the results. Detailed examination and description of multiple parameters of differences in hair was greatly facilitated by the ability to examine the hairs at high magnification under stable conditions of fixed focal length and subject position utilizing the capabilities of the slitlamp biomicroscope.

The foregoing study was expanded to include 43 patients who had administered unilateral topical latanoprost for greater than 10 weeks and who would be available for additional follow-up. Each patient of the 43 patients in the study had glaucoma and treatment consisted of one unilateral drop of latanoprost daily. Mean treatment duration was 19.8±6.1 weeks, range (11–40). No consistent pattern of other topical or systemic medication use was identified. Evidence of hypertrichosis was observed in the region of the treated eye in each of the subjects; 38 Caucasian, 3 African-American, 1 Asian, 1 Hispanic; 13 male, 30 female; average age 65±13, range (36–84). Slitlamp photographs were made of the region of the control eye and treated eye in each patient.

Increased numbers of lashes were present in preexisting lash rows and in some patients additional rows of lashes were seen in the upper and lower lid of the latanoprost treated eye. Increased lash size involving both length and thickness was also apparent in both the upper and lower lids of the treated eye. Several patients had a striking curling of the lashes of the treated compared with the untreated control eye.

The lower lids generally had fewer rows of lashes and the lashes were also less curled than in the upper lids making comparative measurements of the lashes of the lower lid lashes feasible. Accordingly, calipers were used to measure the length of longest lashes of the lower lids in 30 patients. Mean lower lid lash length was 5.83±76 mm in the control eye versus 6.95±91 mm in the treated eye (p<0.0001), (unpaired t-test, Statview statistics program). This represents a 19.5% increased lash length in the treated eye, range (0–36%). Two patients who had no measurable lash length change exhibited increased numbers of lashes.

In the treated eye, lash-like hair growth was observed in several patients in areas adjacent to the region of normal lash distribution. Hairs in the control eye were a mixture of vellus and intermediate-type in the areas of transition between the terminal lashes along the lash line and the vellus hair of the skin. Hairs in the same location in the treated eye had a more robust appearance, were longer, thicker, more pigmented and arose at a more acute angle from the skin than in the control eye, imparting the appearance of a partial new row of terminal lashes.

In the medial and lateral canthal area where vellus and intermediate hairs were present in the control eye, a number of patients had a greater abundance of thicker, longer more pigmented terminal hairs in the same area of the treated eye. Although not grossly visible, with slitlamp examination the vellus hair of the skin of the lateral portion of the lower lid was generally more abundant, longer, thicker and darker in the treated eye. Pigmentation of the lashes and associated hairs was regularly greater in the treated eye than in the control eye and was more obvious in patients who had brown or black hair. (Patients who exhibited hypertrichosis with latanoprost were removed from further drug administration.)

Example 2

Length of Treatment

Eighty-nine subjects were treated as generally described in Example 1 by topical application of latanoprost at a dosage of 1.5 µg/ml/eye/day. Five of the subjects (2 male, 3 female, average age 72 years, all Caucasian) received treatment for a total period of less than 21 days (2, 3, 5, 12 and 17 days, respectively). Follow-up evaluation occurred in ascending order of treatment duration at 13, 14, 5, 6 and 4 months, respectively. The results were compared with the remainder of the subjects who received treatment for greater than 21 days.

In the 5 patients treated briefly, increased number, length, thickness, and pigmentation of lashes occurred and was similar to findings following unilateral sustained treatment. There was no obvious correlation between appearance and duration of treatment except in 3 patients who took latanoprost for <5 days. Each had marked curling of lashes, which was non-uniform in direction and degree, in contrast to the occasional more modest uniform curling seen with sustained treatment. In each patient treated briefly, lash changes persisted to some degree throughout the duration of the follow-up interval.

Brief (less than 21 days), low total dosage (3–25.5 µg) topical latanoprost treatment appears to cause increased lash numbers and altered differentiation involving hypertrophy and hyperpigmentation. Marked irregular curling was observed with <5 days treatment and may result from non-uniform penetration into the hair follicle. Residual evidence of unilateral lash changes following brief treatment may persist for up to 14 months, suggesting a prolongation of the hair cycle (normally about 5 months) or an effect that lasts from one hair cycle to the next.

Example 3

Topical Cream

A topical cream is prepared as follows: Tegacid and spermaceti are melted together at a temperature of 70–80° C. Methylparaben is dissolved in about 500 gm of water and propylene glycol, polysorbate 80, and 13,14-dihydro-15-dehydro-17-phenyl-18,19,20-trinor-PGF$_2\alpha$ isopropyl ester are added in turn, maintaining a temperature of 75–80° C. The methylparaben mixture is added slowly to the Tegacid and spermaceti melt, with constant stirring. The addition is continued for at least 30 minutes with additional stirring until the temperature has dropped to 40–45° C. Finally, sufficient water is added to bring the final weight to 1000 gm and the preparation stirred to maintain homogeneity until cooled and congealed.

The composition is applied to bald human scalp three times a day to stimulate the growth of hair.

Example 4

Topical Cream

A topical cream is prepared as follows: Tegacid and spermaceti are melted together at a temperature of 70–80° C. Methylparaben is dissolved in water and propylene glycol, polysorbate 80, and 13,14-dihydro-15-dehydro-17-phenyl-18,19,20-trinor-PGF$_2\alpha$ isopropyl ester are added in turn, maintaining a temperature of 75–80° C. The methylparaben mixture is added slowly to the Tegacid and spermaceti melt, with constant stirring. The addition is continued for at least 30 minutes with additional stirring until the temperature has dropped to 40–45° C. Finally, sufficient water is added to bring the final weight to 1000 gm and the preparation stirred to maintain homogeneity until cooled and congealed.

The composition is applied to bald human scalp once daily to stimulate the growth of hair.

Example 5

Topical Ointment

An ointment containing 2% by weight 13,14-dihydro-15-dehydro-17-phenyl-18,19,20-trinor-PGF$_2\alpha$ is prepared as follows:

White petrolatum and wool fat are melted, strained and liquid petrolatum is added thereto. The 13,14-dihydro-15-dehydro-17-phenyl-18,19,20-trinor-PGF$_2\alpha$ isopropyl ester, zinc oxide, and calamine are added to the remaining liquid petrolatum and the mixture milled until the powders are finely divided and uniformly dispersed. The mixture is stirred into the white petrolatum, melted and cooled with stirring until the ointment congeals.

The foregoing ointment can be applied topically to mammalian skin for increased rate of hair growth, and can be prepared by omitting the zinc oxide and calamine.

Example 6

Ointment

A dermatological ophthalmic ointment containing 10% by weight 13,14-dihydro-15-dehydro-17-phenyl-18,19,20-trinor-PGF$_2\alpha$ isopropyl ester is prepared by adding the active compound to light liquid petrolatum. White petrolatum is melted together with wool fat, strained, and the temperature adjusted to 45–50° C. The liquid petrolatum slurry is added and the ointment stirred until congealed. Suitably the ointment is packaged in 30 gm tubes.

The foregoing ointment can be applied to the eyelid to enhance the growth of eyelashes. Similarly the composition can be applied to the brow for eyebrow growth.

Example 7

Solution

An aqueous solution containing 5% by weight 13,14-dihydro-15-dehydro-17-phenyl-18,19,20-trinor-PGF$_2\alpha$ isopropyl ester is prepared as follows. The ingredient is dissolved in water and the resulting solution is sterilized by filtration. The solution is aseptically filled into sterile containers.

The composition so prepared can be used in the topical treatment of baldness by application to the scalp daily.

Example 8

Lotion

A sample of 13,14-dihydro-15-dehydro-17-phenyl-18,19,20-trinor-$PGF_2\alpha$ isopropyl ester is dissolved in the vehicle of N-methyl pyrrolidone and propylene glycol. The composition can be used for application to dogs or cats having hair loss due to mange or alopecia of other causes.

Example 9

Aerosol

An aerosol containing approximately 0.1% by weight 13,14-dihydro-15-dehydro-17-phenyl-18,19,20-trinor-$PGF_2\alpha$ isopropyl ester is prepared by dissolving the 13,14-dihydro-15-dehydro-17-phenyl-18,19,20-trinor-$PGF_2\alpha$ in absolute alcohol. The resulting solution filtered to remove particles and lint. This solution is chilled to about minus 30° C. To the solution is added a chilled mixture of dichlorodifluoromethane and dichlorotetrafluoroethane. Thirteen ml plastic-coated amber bottles are cold filled with 11.5 gm each of the resulting solution and capped.

The composition can be sprayed on the scalp daily to stimulate the growth of hair.

Example 10

Dusting Powder

A powder of the compound 13,14-dihydro-15-dehydro-17-phenyl-18,19,20-trinor-$PGF_2\alpha$ isopropyl ester is prepared by mixing in dry form with talcum powder at a weight/weight ratio of 1:10. The powdered mixture is dusted on the fur of minks or other commercially valuable fur bearing animals and show animals for increased rate of hair growth.

Example 11

Related Compounds

Following the procedure of the preceding Examples, compositions are similarly prepared substituting an equimolar amount of a compound of Table 1 for the 13,14-dihydro-15-dehydro-17-phenyl-18,19,20-trinor-$PGF_2\alpha$ isopropyl ester disclosed in the preceding Examples. Similar results are obtained.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for stimulating hair growth in a mammalian species comprising the application to mammalian skin of an effective amount of a prostaglandin PGF compound wherein the alpha chain of the compound has the formula:

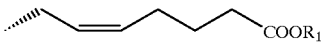

in which $R_1$ is H or an alkyl group having from 1 to 10 carbon atoms; and the omega chain of the compound has the formula:

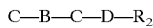

wherein C is a carbon atom or lower alkyl chain, optionally substituted with one or more —OH groups;

B is a single bond, a double bond or a triple bond;

D is a chain having from 1 to 10 carbon atoms, optionally substituted with one or more —OH groups; and $R_2$ is H; a phenyl group having none, one or more substituents selected from the group consisting of $C_1$–$C_5$ alkyl groups, $C_1$–$C_5$ haloalkyl groups, $C_1$–$C_4$ alkoxy groups, $C_1$–$C_4$ haloalkoxy groups, trifluoromethyl groups, $C_1$–$C_3$ aliphatic acylamino groups, nitro groups, halogen atoms, and phenyl groups; an aromatic heterocyclic group having 5–6 ring atoms; or a cycloalkane or a cycloalkene with 3–7 carbon atoms in the ring, optionally substituted with lower alkyl groups with 1–5 carbon atoms;

or a pharmacologically acceptable acid addition salt thereof.

2. The method of claim 1 wherein the concentration of the compound applied is from about 0.0000001% to about 50% by weight of the composition.

3. The method of claim 1 wherein the compound is a $PGF_2\alpha$ derivative.

4. The method of claim 3 wherein the compound is 13,14-dihydro-15-dehydro-17-phenyl-18,19,20-trinor-$PGF_2\alpha$ isopropyl ester or a pharmaceutically acceptable salt thereof.

5. A method for the conversion of vellus hair or intermediate hair to growth as terminal hair comprising the application to mammalian skin at the locale of vellus hair of an effective amount of a prostaglandin PGF compound wherein the alpha chain of the compound has the formula:

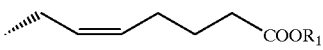

in which $R_1$ is H or an alkyl group having 1 to 10 carbon atoms, especially 1 to 6 atoms, for instance methyl, ethyl, propyl, isopropyl, butyl, isobutyl, neopentyl or benzyl or a derivative giving the final substance equivalent properties as a hair growth stimulating agent; and the omega chain of the compound has the formula:

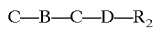

wherein C is a carbon atom or lower alkyl chain, optionally substituted with one or more —OH groups;

B is a single bond, a double bond or a triple bond;

D is a chain having from 1 to 10 carbon atoms, optionally substituted with one or more —OH groups; and $R_2$ is H; a phenyl group having none, one or more substituents selected from the group consisting of $C_1$–$C_5$ alkyl groups, $C_1$–$C_5$ haloalkyl groups, $C_1$–$C_4$ alkoxy groups, $C_1$–$C_4$ haloalkoxy groups, trifluoromethyl groups, $C_1$–$C_3$ aliphatic acylamino groups, nitro groups, halogen atoms, and phenyl groups; an aromatic heterocyclic group having 5–6 ring atoms; or a cycloalkane or a cycloalkene with 3–7 carbon atoms in the ring, optionally substituted with lower alkyl groups with 1–5 carbon atoms;

or a pharmacologically acceptable acid addition salt thereof.

6. The method of claim 5 wherein the concentration of the compound applied is from about 0.0000001% to about 50% by weight of the composition.

7. The method of claim 5 wherein the compound is a $PGF_2\alpha$ derivative.

8. The method of claim 7 wherein the compound applied is 13,14-dihydro-15-dehydro-17-phenyl-18,19,20-trinor-$PGF_2\alpha$ isopropyl ester in the form of the free base or acid addition salts thereof.

9. A method for stimulating hair follicles to increase hair growth and one or more properties selected from the group consisting of luster, sheen, brilliance, gloss, glow, shine or patina of hair associated with the follicles, comprising the application to mammalian skin at the locale of the follicles of an effective amount of a prostaglandin PGF compound wherein the alpha chain of the compound has the formula:

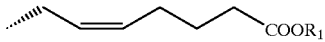

in which $R_1$ is H or an alkyl group having 1 to 10 carbon atoms, especially 1 to 6 atoms, for instance methyl, ethyl, propyl, isopropyl, butyl, isobutyl, neopentyl or benzyl or a derivative giving the final substance equivalent properties as a hair growth stimulating agent; and the omega chain of the compound has the formula:

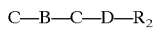

wherein C is a carbon atom or lower alkyl chain, optionally substituted with one or more —OH groups;

B is a single bond, a double bond or a triple bond;

D is a chain having from 1 to 10 carbon atoms, optionally substituted with one or more —OH groups; and $R_2$ is H; a phenyl group having none, one or more substituents selected from the group consisting of $C_1$–$C_5$ alkyl groups, $C_1$–$C_5$ haloalkyl groups, $C_1$–$C_4$ alkoxy groups, $C_1$–$C_4$ haloalkoxy groups, trifluoromethyl groups, $C_1$–$C_3$ aliphatic acylamino groups, nitro groups, halogen atoms, and phenyl groups; an aromatic heterocyclic group having 5–6 ring atoms; or a cycloalkane or a cycloalkene with 3–7 carbon atoms in the ring, optionally substituted with lower alkyl groups with 1–5 carbon atoms;

or a pharmacologically acceptable acid addition salt thereof.

* * * * *

(12) EX PARTE REEXAMINATION CERTIFICATE (7640th)
United States Patent
Johnstone

(10) Number: US 6,262,105 C1
(45) Certificate Issued: Jul. 27, 2010

(54) METHOD OF ENHANCING HAIR GROWTH

(76) Inventor: Murray A. Johnstone, 1221 Madison, #1124, Seattle, WA (US) 98104

Reexamination Request:
No. 90/009,431, Mar. 10, 2009

Reexamination Certificate for:
Patent No.: 6,262,105
Issued: Jul. 17, 2001
Appl. No.: 09/366,656
Filed: Aug. 3, 1999

Related U.S. Application Data

(63) Continuation of application No. PCT/US98/02289, filed on Feb. 3, 1998.
(60) Provisional application No. 60/037,237, filed on Feb. 4, 1997.

(51) Int. Cl.
*A61K 8/30* (2006.01)
*A61K 8/37* (2006.01)
*A61K 8/365* (2006.01)
*A61K 31/557* (2006.01)
*A61K 31/5575* (2006.01)
*A61Q 7/00* (2006.01)

(52) U.S. Cl. .................. 514/430; 514/530; 514/880
(58) Field of Classification Search .................. None
See application file for complete search history.

(56) References Cited

U.S. PATENT DOCUMENTS 5,296,504 A    3/1994    Stjernschantz et al.
5,422,369 A    6/1995    Stjernschantz et al.

FOREIGN PATENT DOCUMENTS

WO    95/11003    4/1995

OTHER PUBLICATIONS

"Effects on Intraocular Pressure and Side Effects of 0.005% Latanoprost Applied One Daily, Evening or Morning" by Alm et al. Ophthalmology vol. 102, No. 12 at 1743–52, published Dec. 1995, 10 pages.
"A Six–Month, Randomized, Double–masked Studying Comparing Latanoprost with Timolol in Open–angle Glaucoma and Ocular Hypertension," by Watson et al. Ophthalmology vol. 103 at 126–137, publsihed Jan. 1, 1996, 12 pages.

*Primary Examiner*—Gary L Kunz

(57) ABSTRACT

Methods and compositions for stimulating the growth of hair are disclosed containing prostaglandins, derivatives or analogues thereof for use in treating the skin or scalp of a human or non-human animal. Prostaglandins of the $A_2$, $F_2\alpha$ and $E_2$ types are preferred for this treatment method.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-9 is confirmed.

\* \* \* \* \*